US00PP14575P29

(12) United States Plant Patent
Kordes

(10) Patent No.: US PP14,575 P2
(45) Date of Patent: Mar. 9, 2004

(54) MINIATURE ROSE PLANT NAMED 'KORLONEK'

(50) Latin Name: *Rosa hybrida*
Varietal Denomination: KORlonek

(75) Inventor: Tim-Hermann Kordes, Offenseth-Sparrieshoop (DE)

(73) Assignee: W. Kordes Sohne Rosenschulen GmbH & Co. KG (DE)

( * ) Notice: Subject to any disclaimer, the term of this patent is extended or adjusted under 35 U.S.C. 154(b) by 31 days.

(21) Appl. No.: 09/992,514

(22) Filed: Nov. 6, 2001

(51) Int. Cl.[7] ..... A01H 5/00
(52) U.S. Cl. ..... Plt./122
(58) Field of Search ..... Plt./122

*Primary Examiner*—Bruce R. Campell
*Assistant Examiner*—W C Haas
(74) *Attorney, Agent, or Firm*—Webb Ziesenheim Logsdon Orkin & Hanson, P.C.

(57) ABSTRACT

A new miniature rose plant which has abundant, red colored flowers and attractive foliage. The variety successfully propagates from softwood cuttings and is suitable for year round production in commercial glasshouses as a flowering pot plant.

2 Drawing Sheets

BOTANICAL CLASSIFICATION

*Rosa hybrida.*

BACKGROUND OF THE NEW PLANT

The present invention constitutes a new and distinct variety of miniature rose plant which was developed by artificially pollinating an unnamed seedling (unpatented) with an unnamed seedling (unpatented).

The objective of the hybridization of this rose variety for commercial greenhouse culture was to create a new and distinct variety with:

1. Uniform and abundant flowers with good keepability;
2. Attractive long lasting foliage and compact growth;
3. Year round flowering under glasshouse conditions;
4. Suitability for production from softwood cuttings in pots; and
5. Durable flowers and foliage which make the variety suitable for distribution in the floral industry.

This combination of qualities was not present in previously available commercial cultivars of this type and distinguish 'KORlonek' from other varieties.

The two parents were crossed in the summer of 1999 and the resulting seed was sown in December 1999 in a controlled glasshouse environment. The seeds from hybridization were planted in a controlled environment in Klein Offenseth, Sparrieshoop, Germany and evaluations were conducted on the resulting plants.

SUMMARY OF THE INVENTION

Asexual reproduction of 'KORlonek' by softwood cuttings was first done in Denmark and later in California in controlled greenhouse environments. The characteristics of the new variety remain true to type through successive propagations.

The new rose variety may be distinguished from its seed parent, an unnamed breeding seedling, by the following combination of characteristics:

1. 'KORlonek' has medium double flowers, while the seed parent has small single flowers.
2. 'KORlonek' has red colored petals, while the seed parent has light orange petals.

The new variety may be distinguished from its pollen parent, an unnamed breeding seedling, by the following combination of characteristics:

1. 'KORlonek' has bigger flowers and foliage as compared to the pollen parent.
2. 'KORlonek' has red colored petals, while the pollen parent has dark pink petals.

The new variety differs from 'KORfrauma', U.S. Plant Pat. No. 11,363, as set forth in Table 1:

TABLE 1

| | 'KORlonek' | 'KORfrauma' |
|---|---|---|
| Petal color, upper surface | Red Group 45B | Red Group 43A |
| Petal color, reverse surface | Red Group 45A–B | Red Group 53B |
| Petal count | 50–55 petals | 30–35 petals |

DESCRIPTION OF THE DRAWINGS

The accompanying color illustrations show as true as is reasonably to obtain in color photographs of this type, the typical characteristics of the buds, flowers, leaves, stems of 'KORlonek'.

In photo sheet # 1.

Figures 1, 2, 3, 4, 5, 6, 7, 8, 9:
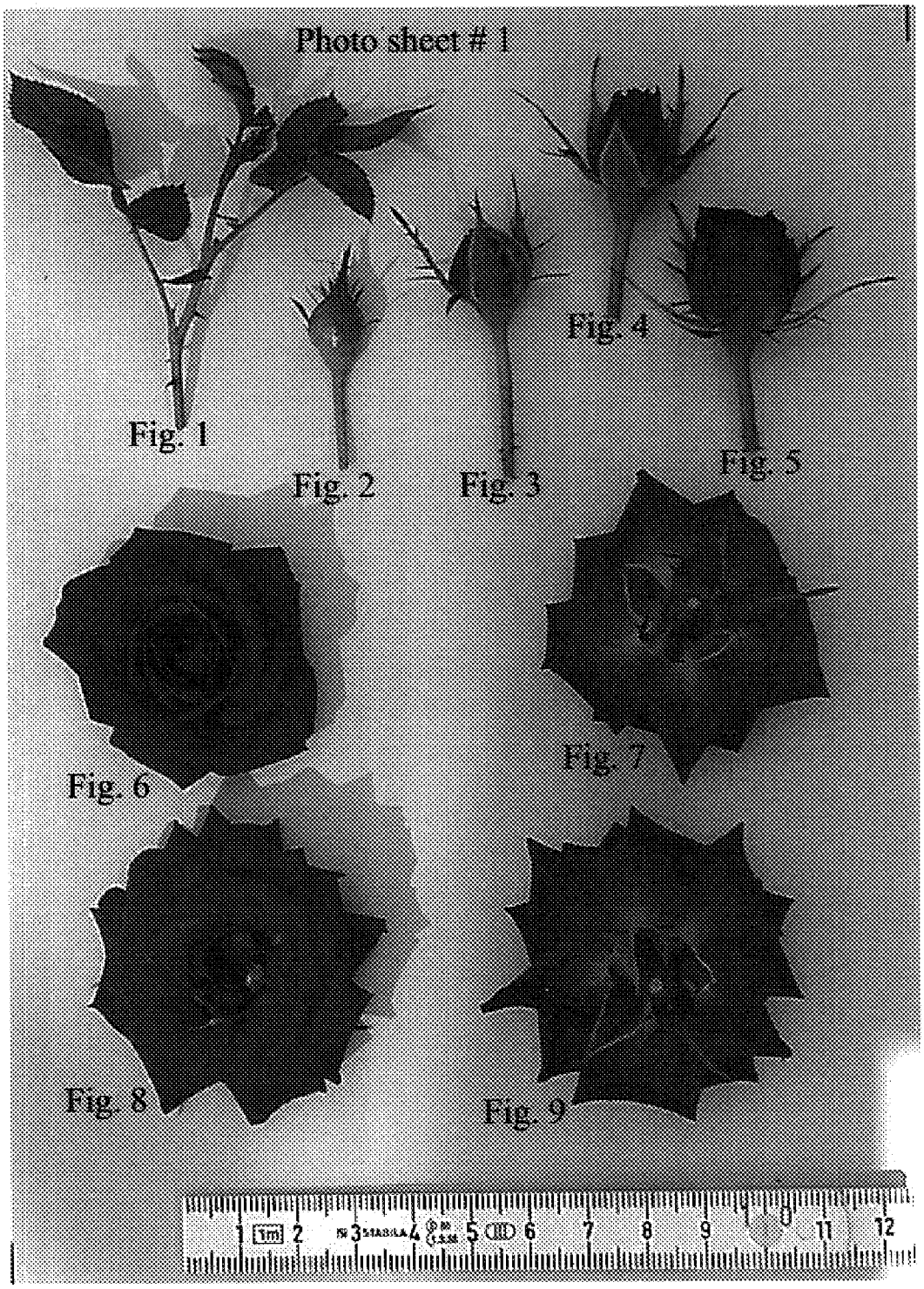
FIG. 1 shows a young shoot.
FIG. 2 shows a bud before opening the sepals.
FIG. 3 shows a bud at the opening of the sepals.
FIG. 4 shows a bud at the opening of the petals.
FIG. 5 shows a flower during course of opening.
FIG. 6 shows an open flower, obverse plan view.
FIG. 7 shows an open flower, reverse plan view.
FIG. 8 shows a fully open flower, obverse plan view.
FIG. 9 shows a fully open flower, reverse plan view.
Figures 10, 11, 12, 13, 14, 15, 16, 17, 18:
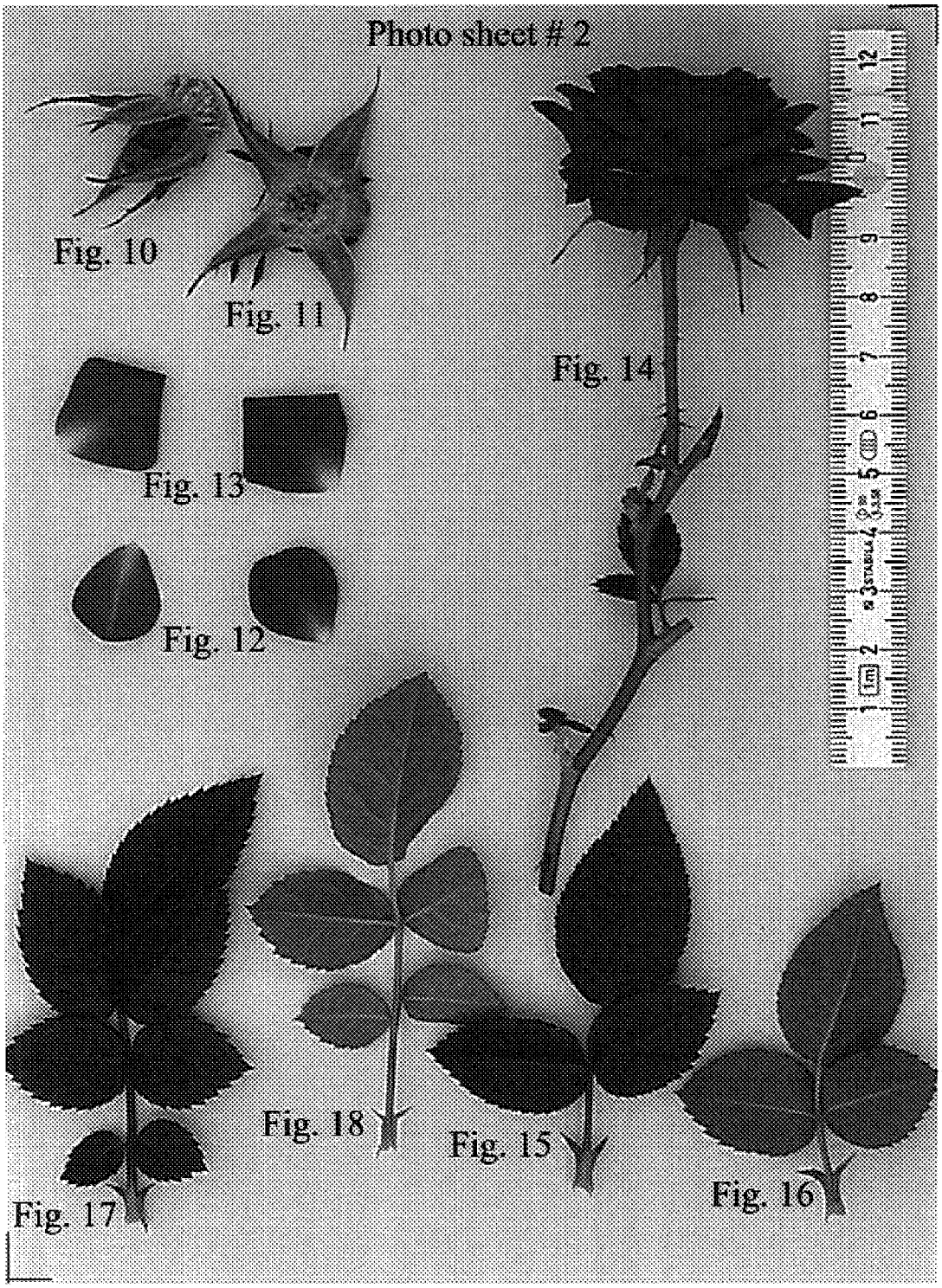

In photo sheet # 2:

FIG. 10 shows a receptacle with stamens and pistils.

FIG. 11 shows a receptacle with pistils and stamens removed.

FIG. 12 shows detached flower petals, outer surface.

FIG. 13 shows detached flower petals, inner surface.

FIG. 14 shows a bare stem exhibiting thorns and flower attachment.

FIG. 15 shows three leaflets, upper side.

FIG. 16 shows three leaflets, under side.

FIG. 17 shows five leaflets, upper side.

FIG. 18 shows five leaflets, under side.

DESCRIPTION OF THE NEW PLANT

The following is a detailed description of 'KORlonek', as observed in its growth in greenhouses in Fraugde, Denmark, and greenhouses in Santa Barbara Calif. both at 20–25° C.

Descriptions were made from plants 11 to 13 weeks old after propagation produced in a pot treated with growth regulators normally used in the greenhouse production process. The growth regulator Paclobutrazol was applied at 15–30 ppm weekly beginning at a plant age of 8 weeks. The peduncle lengths mentioned may actually be shorter and the foliage color several shades darker than on untreated specimens. Color references are made using The Royal Horticultural Society (London, England) Colour Chart, 1995, except where common terms of color are used.

THE PLANT

Classification:
- *Botanical.*—*Rosa hybrida.*
- *Commercial.*—Miniature.

Plant growth: Moderately vigorous. Grows compact upright to bushy. When grown as 10 cm pot plant, the average height of the plant itself is 18–20 cm, and average width is 20 cm. When grown as a 15 cm pot plant, the average height of the plant itself is 22–27 cm, and average width is 30 cm. Production time is generally 11 to 13 weeks depending on average temperature, light level, and cultural practices.

Stem:
- *Color.*—Young wood: Yellow-Green Group 145A with intonations of Greyed-Red Group 178A. Older wood: Yellow-Green Group 146C.
- *Thorns.*—Incidence: High number of thorns. Size: 4–5 mm. Color: Greyed-Red Group 178C. Shape: Hooked downwards.
- *Surface.*—Young wood: Smooth. Older wood: Smooth.
- *Stem diameter.*—2–3 mm.
- *Internode length.*—25–30 mm.
- *Numbers of internodes.*—7–8.

FOLIAGE

Arrangement: Alternate, compound with 3–7 leaflets per leaf, generally symmetrical, abundant, and flat in aspect. Stipules at petiole base.

Quantity of leaves: 7–8 per lateral branch.

Leaf size:
- *Length.*—65–70 mm.
- *Width.*—50–55 mm.

Petioles:
- *Color.*—Yellow-Green Group 146A.
- *Margin.*—Entire, no prickles.
- *Length.*—10–15 mm.
- *Diameter.*—About 1 mm.

Stipules:
- *Size.*—5–6 mm.
- *Surface.*—Smooth.
- *Margin.*—Entire.
- *Color.*—Green Group 141D.

Rachis:
- *Color.*—Green Group 141D with intonations of Greyed-Red Group 178B.
- *Margin.*—Entire
- *Length.*—10–25 mm.

Leaflets:
- *Margin.*—Serrated.
- *Shape.*—Ovate with acute apex and obtuse base.
- *Texture.*—Smooth.
- *Appearance.*—Glossy.
- *Size.*—Length: 10–35 mm. Width: 7–25 mm.
- *Color.*—Young foliage: Upper surface: Yellow-Green Group 146A, edge with intonations of Greyed-Purple Group 178B. Lower surface: Yellow-Green Group 148C, with intonations of Greyed-Purple Group 178B. Mature foliage: Upper surface: Yellow-Green Group 137A. Lower surface: Greyed-Green Group 191A.

INFLORESCENCE

Blooming habit: Recurrent.

Number of flowers: Generally 1 bud per flowering stem.

Peduncle:
- *Color.*—Yellow-Green Group 144C.
- *Texture.*—Smooth, with hairs/prickles colored Greyed-Red Group 178A.
- *Length.*—30–35 mm.
- *Strength.*—Upright.

Receptacle:
- *Surface.*—Smooth, glabrous.
- *Shape.*—Funnel-shaped.
- *Size.*—Height: 6–7 mm. Width: 5–6 mm.
- *Color.*—Green Group 143B.

Sepals:
- *Quantity.*—5.
- *Shape.*—Narrowly ovate with acute tip.
- *Texture.*—Smooth, with slightly pubescence.
- *Margin.*—Foliaceous appendages on three of the five sepals.
- *Appearance.*—Dull.
- *Color.*—Upper surface: Green Group 143A. Reverse surface: Yellow-Green Group 146B.

Buds:
- *Size when just opening.*—Height: 18–24 mm. Width: 14–17 mm.
- *Shape.*—Pointed.
- *Color.*—Red Group 45A at one-fourth open.

Flower:
- *Duration.*—As a pot plant, flowers last 11–19 days.
- *Fragrance.*—None.
- *Size.*—50–55 mm in diameter.
- *Form* (*shape of flower when viewed from the side*).—Upon opening: Cupped. Open flower: Cupped.
- *Color.*—Petals, upon opening: Upper surface: Red Group 43B. Reverse surface: Red Group 43A–B. Petals, after opening: Upper surface: Red Group 45C, with intonations of Red Group 43B. Reverse surface: Red Group 45C.

*Basal petal spots.*—Size: 2–3 mm. Color: Yellow-Orange Group 12D.

*General tonality of open flower.*—Red Group 41A at third day fading to Red Group 52A.

Petals:

*Petal reflex.*—Generally straight. Outermost petals reflex backwards.

*Texture.*—Smooth and satiny.

*Petal edge.*—Uniform.

*Petal count.*—Approximately 35–40 per flower.

*Petal size.*—Length: 20–25 mm. Width: 18–20 mm.

*Shape.*—Outer petals: Ovate to round. Inner petals: Ovate.

*Petaloids.*—Generally none.

Reproductive organs:

*Stamens.*—Number: Approximately 50–60 per flower. Pollen: Color: Greyed-Orange Group 167A. Abundance: Average. Anthers: Size: 1.5 mm. Color: Greyed-Orange Group 167A. Shape: Oblong. Abundance: Average. Filaments: Size: 2–3 mm. Color: Greyed-Yellow Group 162A.

*Pistils.*—Number: Approximately 30–35 per flower.

*Stigmas.*—Location: Below in location to anthers. Color: Greyed-Yellow Group 160A.

*Styles.*—Color: Greyed-Yellow Group 160A. Length: 4–6 mm.

GROWTH

Vegetation: Dense.

Blooming: Abundant.

Aptitude to bear fruit: Poor.

Resistance to diseases: Above average resistance to mildew and Botrytis under normal growing conditions in Fraugde, Denmark and Santa Barbara, Calif.

Hips/seeds: Unknown, the plant has never been grown to the stage of seed development due to the fact that the variety is developed for use as a flowering potted plant only.

Winter hardiness and drought/heat tolerance: This variety is a potted flowering plant developed for one time use only and has not been tested for winter hardiness or drought/heat tolerance.

I claim:

1. A new and distinct variety of rose plant substantially as shown and described.

* * * * *

Photo sheet # 1

Photo sheet # 2